United States Patent [19]

Grabstein et al.

[11] Patent Number: 5,552,303

[45] Date of Patent: Sep. 3, 1996

[54] DNA ENCODING EPITHELIUM-DERIVED T-CELL FACTOR

[75] Inventors: Kenneth Grabstein, Mercer Island; Dirk Anderson; June Eisenman, both of Seattle; Victor Fung, Redmond; Charles Rauch, Bainbridge Island, all of Wash.

[73] Assignee: Immunex Corporation, Seattle, Wash.

[21] Appl. No.: 31,399

[22] Filed: Mar. 8, 1993

[51] Int. Cl.⁶ .......................... C12P 21/06; C12N 15/24; C12N 5/10; C07K 14/54

[52] U.S. Cl. .................. 435/69.51; 435/320.1; 435/240.1; 536/23.52; 530/351

[58] Field of Search ............... 435/69.52, 69.5, 435/240.1, 243, 25.23, 254, 255, 320.1; 536/23.1, 23.5; 530/351

[56] References Cited

PUBLICATIONS

McMahan et al., "A Novel IL-1 receptor, cloned from B cells by mammalian expression, is expressed in many cell types", *EMBO J.* 10:2821–2832 (1991).

Nishimura et al 1991 FEBS Lett 281:167–169.

Coleman et al, *J. Immunol* 138, 1987, pp. 3314–3318.

Cornaglia–Ferraris et al, Lymphokine Res. 4(3) 1985, pp. 251–263.

Ogata et al, *J. Leukocyte Biol* 49, 1989, pp. 69–78.

*Primary Examiner*—Charles L. Patterson, Jr.
*Assistant Examiner*—Karen Cochrane Carlson
*Attorney, Agent, or Firm*—Seed and Berry LLP

[57] ABSTRACT

There is disclosed a mammalian epithelium-derived T-cell factor (EFT) polypeptide, derivatives thereof, DNA sequences, recombinant DNA molecules and transformed host cells that produce ETF polypeptides. More particularly, this invention provides isolated mammalian ETF polypeptides and derivatives thereof that regulate events in T-lymphocyte proliferation.

21 Claims, 5 Drawing Sheets

FIGURE 1

```
AAC TGG GTG AAT GTA ATA AGT GAT TTG AAA AAA ATT GAA GAT CTT ATT
Asn Trp Val Asn Val Ile Ser Asp Leu Lys Lys Ile Glu Asp Leu Ile

CAA TCT ATG CAT ATT GAT GCT ACT TTA TAT ACA GAA AGT GAT GTT CAC
Gln Ser Met His Ile Asp Ala Thr Leu Tyr Thr Glu Ser Asp Val His

CCC AGT TGC AAG GTA ACA GCA ATG AAG TGC TTT ACA GAA TTG GAG CAA
Pro Ser Cys Lys Val Thr Ala Met Lys Cys Phe Thr Glu Leu Glu Gln

GTT ATT TCA CAT GAG TCC GGA GAT ACA GAT ATT CAT GAT ACA GTA GAA
Val Ile Ser His Glu Ser Gly Asp Thr Asp Ile His Asp Thr Val Glu

AAT CTT ATC CTA GCA AAC AAC ATC TTG TCT TCT AAT GGG AAT ATA
Asn Leu Ile Leu Ala Asn Asn Ile Leu Ser Ser Asn Gly Asn Ile

ACA GAA TCT GGA TGC AAA GAA TGT GAG CTA GAG GAG AAA AAT ATT
Thr Glu Ser Gly Cys Lys Glu Cys Glu Leu Glu Glu Lys Asn Ile

AAA GAA TTT TTG CAG AGT TTT GTA CAT ATT GTC CAA ATG TTC ATC AAC
Lys Glu Phe Leu Gln Ser Phe Val His Ile Val Gln Met Phe Ile Asn

ACT TCT TGA
Thr Ser
```

FIGURE 2

```
AAC TGG GTG AAT GTA ATA AGT GAT TTG AAA AAA ATT GAA GAT CTT ATT
Asn Trp Val Asn Val Ile Ser Asp Leu Lys Lys Ile Glu Asp Leu Ile

CAA TCT ATG CAT ATT GAT GCT ACT TTA TAT ACG GAA AGT GAT GTT CAC
Gln Ser Met His Ile Asp Ala Thr Leu Tyr Thr Glu Ser Asp Val His

CCC AGT TGC AAA GTA ACA GCA ATG AAG TGC TTT CTC TTG GAG TTA CAA
Pro Ser Cys Lys Val Thr Ala Met Lys Cys Phe Leu Leu Glu Leu Gln

GTT ATT TCA CTT GAG TCC GGA GAT GCA AGT ATT CAT GAT ACA GTA GAA
Val Ile Ser Leu Glu Ser Gly Asp Ala Ser Ile His Asp Thr Val Glu

AAT CTG ATC CTA GCA AAC AAC AGT TTG TCT TCT AAT GGG AAT GTA ATT
Asn Leu Ile Leu Ala Asn Asn Ser Leu Ser Ser Asn Gly Asn Val Ile

ACA GAA TCT GGA TGC AAA GAA TGT GAG GAA CTG GAG GAA AAA TTC ATC
Thr Glu Ser Gly Cys Lys Glu Cys Glu Glu Leu Glu Glu Lys Phe Ile

AAA GAA TTT TTG CAG AGT TTT GTA CAT ATT GTC CAA ATG TTC ATC AAC
Lys Glu Phe Leu Gln Ser Phe Val His Ile Val Gln Met Phe Ile Asn

ACT TCT TGA
Thr Ser
```

FIGURE 4

```
ATGAGAATTTCGAAACCACATTTGAGAAGTATTTCCATCCAGTGCTACTT
||||||||||||||||||||||||||||||||||||||||||||||||| |
ATGAGAATTTCGAAACCACATTTGAGAAGTATTTCCATCCAGTGCTACCT

GTGTTACTTCTAAACAGTCATTTCTAACTGAAGCTGGCATTCATGTCT
|||||||||||||| |||||||||||||||||||||||||||||||||
GTGTTACTTCTAAGAGTCATTTCTAACTGAAGCTGGCATTCATGTCT

TCATTTGGGCTGTTTCAGTGCAGGGCTTCCTAAAACAGAAGCCAACTGG
||||||||||||||||||||||||||| |||||||||||||||||||||
TCATTTGGGCTGTTTCAGTGCAGGGCTCCCTAAAACAGAAGCCAACTGG

GTGAATGTAATAAGTGATTTGAAAAAATTGAAGATCTTATTCAATCTAT
|||||||||||||||||||||||||||||||||||||||||||||||||
GTGAATGTAATAAGTGATTTGAAAAAATTGAAGATCTTATTCAATCTAT

GCATATTGATGCTACTTTATATACGGAAAGTGATGTTCACCCAGTTGCA
||||||||||||||||||||||||| |||||||||||||||||||||||
GCATATTGATGCTACTTTATATACAGAAAGTGATGTTCACCCAGTTGCA

AAGTAACAGCAATGAAGTGCTTTCTCTTGGAGTTACAAGTTATTTCACTT
| |||||||||||||||||||||||||||||||| ||||||||||||| |
AGGTAACAGCAATGAAGTGCTTTCTCTTGGAGTTGCAAGTTATTTCACAT

GAGTCCGGAGATGCAAGTATTCATGATACAGTAGAAAATCTGATCATCCT
|||||||||| ||  |||||||||||||||||||||||||| |||||||
GAGTCCGGAGATACAGATATTCATGATACAGTAGAAAATCTTATCATCCT

AGCAAACAACAGTTTGTCTTCTAATGGAATGTAACAGAATCTGGATGCA
||||||||||  ||||||||||||||||||| |||||||||||||||||
AGCAAACAACATCTTGTCTTCTAATGGAATATAACAGAATCTGGATGCA

AAGAATGTGAGGAACTGGAGGAAAAAATATTAAAGAATTTTTGCAGAGT
||||||||||||||||| |||||||||||||||||||||||||||||||
AAGAATGTGAGGAACTAGAGGAAAAAATATTAAAGAATTTTTGCAGAGT

TTTGTACATATTGTCCAAATGTTCATCAACACTTCTTGA
|||||||||||||||||||||||||||||||||||||||
TTTGTACATATTGTCCAAATGTTCATCAACACTTCTTGA
```

FIGURE 5

```
1   MRISKPHLRSISIQCYLCLLLNSHFLTEAGIHVFILGCFSAGLPKTEANW   50
1   MRISKPHLRSISIQCYLCLLLKSHFLTEAGIHVFILGCFSAGLPKTEANW   50

51  VNVISDLKKIEDLIQSMHIDATLYTESDVHPSCKVTAMKCFLLELQVISL   100
51  VNVISDLKKIEDLIQSMHIDATLYTESDVHPSCKVTAMKCFLLELQVISH   100

101 ESGDASIHDTVENLIILANNSLSSNGNVTESGCKECEELEEKNIKEFLQS   150
101 ESGDTDIHDTVENLIILANNILSSNGNITESGCKECEELEEKNIKEFLQS   150

151 FVHIVQMFINTS*   163
151 FVHIVQMFINTS*   163
```

DNA ENCODING EPITHELIUM-DERIVED T-CELL FACTOR

FIELD OF THE INVENTION

The present invention relates generally to a mammalian epithelium-derived T-cell factor ("ETF") polypeptide. It more particularly relates to an isolated cDNA sequence encoding a polypeptide having ETF biological activity and isolated mammalian ETF polypeptide sequences and derivatives and processes for making ETF polypeptides using recombinant DNA technology.

BACKGROUND OF THE INVENTION

T-cells, also known as T-lymphocytes, are a class of immune effector cells. In peripheral tissues, T-cells can be divided into two broad groups based on their mutually exclusive expression of CD4 and CD8 cell surface molecules. Typical CD8+T-cells become cytotoxic T-cells after activation and destroy antigen bearing target cells through direct cell contact. Activated CD4+T-cells generally provide positive signals, for example, "helper" function for B cells (that enable B cells to differentiate into antibody-forming cells) and, therefore, are called helper T-cells.

Six T-cell growth factors have previously been identified. The six are: Interleukin (IL) -2, -4.4, -9, -12 and cofactor IL-10. IL-2's open reading frame codes for a 15 kDa, 153-amino acid polypeptide. IL-2 is produced by certain T-cells and by large granular lymphocytes. IL-2 was originally discovered as a factor that would support long-term growth of human T-cells. In addition to T-cell growth, its effects include activation of natural killer (NK) cells and lymphokine-activated killer (LAK) cells as well as cytotoxic T-cells ("CTL"), macrophages and promotion of B-cell growth.

IL-4 is a 15–20 kDa protein produced by activated T-cells, bone marrow stromal cells, and mast cells. The IL-4 open reading frame codes for 140-amino acid murine IL-4 and 153-amino acid human IL-4. Originally, IL-4 was defined as a factor that activated B-cell growth and differentiation. Its effects also include macrophage activation and induction of class II MHC molecules, growth of some T-cell and mast cell lines, proliferation and CTL generation from human peripheral blood T-cells, enhancement of immunoglobulin production by B-cells, and a cofactor in growth of hematopoietic cells from stem cells. IL-4 plays an important role in the down-regulation of IL-2 induced NK cell and LAK cell activities. Human IL-4 is not active on murine cells.

IL-7 is a 20–25 kDa, 177 amino acid polypeptide produced by bone marrow and thymic stromal cells. Although it was originally described as a pre-B-cell growth factor, IL-7 supports the growth of pro-B-cells as well as pre-B-cells. IL-7 also induces proliferation and CTL generation from human peripheral blood T-cells, IL-2 receptor expression, IL-2 production, and proliferation in CD4+ and CD8+ cells. IL-7 also synergizes with IL-2 and increases thymic T-cell proliferation and induces proliferation of CD4− and CD8− thymocytes.

IL-9 is a 30–40 kDa, 144 amino acid polypeptide produced by activated T-lymphocytes. IL-9 was first identified as a helper T-cell growth factor. IL-9 stimulates erythroid development and enhances IL-3 induced proliferation of bone marrow-derived mast cells. It also modulates IgE and IgG production by B-cells in the presence of IL-4. Murine IL-9 is active on human cells, whereas human IL-9 does not act on murine cells.

Human IL-10 is a 16–20 kDa, 178-amino acid polypeptide produced by macrophages and TH2 but not TH1 T-helper cells. Like IL-2, IL-4 and IL-7, IL-10 has several different biological activities. IL-10 was discovered on the basis of its ability to inhibit cytokine production by activated T-cells. Both human and murine IL-10 are growth-stimulatory cofactors for thymocytes and T-cells in combination with IL-7 or IL-2 plus IL-4. IL-10 stimulates mast cell viability and growth in combination with IL-4 or IL-3 plus IL-4. IL-10 also induces the IgG secretion and expression of MHC class II molecules on B-cells and increases their viability in culture.

IL-12 is constitutive or induced by phorbol ester and calcium ionophore in lymphoblastoid cell lines and is produced by LPS stimulated macrophages. IL-12 has a molecular weight of 70 kDa and an unusual heterodimeric structure, being formed of two disulphide-bonded glycoproteins. The larger of the two glycoprotein subunits is a 40 kDa, 328-amino acid polypeptide. The smaller glycoprotein subunit is a 35 kDa, 253-amino acid polypeptide. Both glycoprotein subunits are necessary for bioactivity. IL-12 induces the proliferation of activated T-cells of both the CD4+ and CD8+ subsets independently of IL-2. IL-12 also activates NK-cell-mediated cytotoxicity and synergizes with IL-2 to generate LAK cells. Unlike IL-2 and IL-7, but similar to IL-4, IL-12 causes little or no proliferation of resting peripheral blood mononuclear cells.

SUMMARY OF THE INVENTION

A novel T-cell growth factor, hereinafter referred to as "epithelium-derived T-cell factor" ("ETF"), has been isolated and purified. A cDNA sequence encoding a simian ETF polypeptide was isolated that has a 483-bp 5' noncoding region preceding an open reading frame of 489 bp and a 303-bp 3' noncoding region. A cDNA sequence encoding a human ETF polypeptide has a 316-bp 5' noncoding region preceding an open reading frame of 489 bp and a 397-bp 3' noncoding region. The nucleotide sequences and deduced amino acid sequences of simian and human open reading frames are disclosed in SEQ ID NOS 1 and 4. Both the simian and human open reading frames encode a precursor polypeptide (SEQ ID NOS 2 and 5). The precursor polypeptides each comprise a 48-amino acid leader sequence and a sequence encoding mature simian or human ETF polypeptides. The active simian and human ETF polypeptides are disclosed in SEQ ID NO 3 and 6, respectively.

The present invention further comprises other ETF polypeptides encoded by nucleotide sequences that hybridize, under moderate to high stringency conditions, to probes defined by nucleotides 145 through 489 of SEQ ID NOS 1 or 4 or to their complementary DNA or RNA strands, and that code on expression for polypeptides that stimulate T-lymphocytes to proliferate and differentiate. The invention further comprises nucleotide sequences that, due to the degeneracy of the genetic code, encode ETF polypeptides encoded by the nucleotide sequences described above and sequences complementary to them.

Further still, the invention provides for recombinant DNA molecules comprising the foregoing nucleotide sequences, for example, expression vectors or plasmids and transformed host cells, that are useful in producing ETF polypeptides, and processes for producing recombinant ETF polypeptides using such molecules.

BRIEF DESCRIPTION OF THE DRAWINGS

FIG. 1 shows the nucleotide sequence and deduced amino acid sequence of the active simian species of ETF.

FIG. 2 shows the nucleotide sequence and deduced amino acid sequence of the active human species of ETF.

FIG. 4 shows the homology between nucleotide sequences encoding human and simian species of ETF. The human sequence is shown above the simian sequence.

FIG. 5 shows the homology between amino acid sequences of human and simian species of ETF. The human sequence is shown above the simian sequence. In both species, the leader sequence (amino acids 1 through 48) is cleaved from the precursor polypeptide to form the mature polypeptide (amino acids 49 through 162).

DETAILED DESCRIPTION OF THE INVENTION

Figure 3:
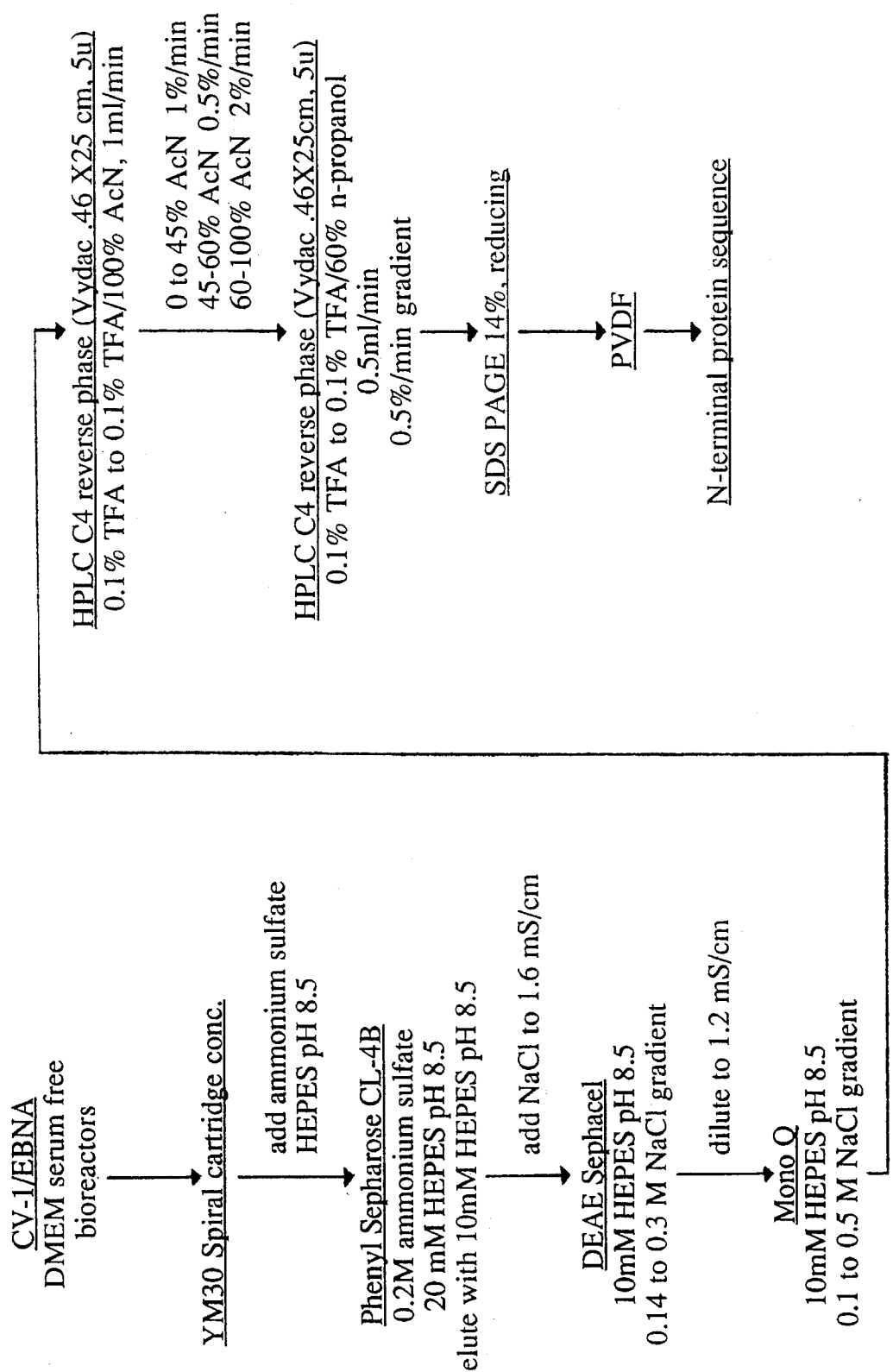
FIG. 3 shows a purification and protein sequencing scheme useful in isolating ETF polypeptides.

"Epithelium-derived T-cell factor" or "ETF" refers to mammalian polypeptides that are structurally similar to the polypeptides disclosed herein and that stimulate T-lymphocytes to proliferate and differentiate. ETF is distinguishable from IL-2, IL-4, IL-7, IL-9, IL-10, and IL-12 in structure and cellular origin (Table 1). In primates, ETF polypeptide is initially produced by epithelial cells as a 162-amino acid precursor ETF polypeptide. This precursor contains a 48-amino acid leader sequence that is removed from the precursor polypeptide to form the mature polypeptide. The mature ETF polypeptide is capable of signaling proliferation and/or differentiation of precursor or mature T-cells. The protein, therefore, can be used to promote long-term in vitro culture of T-lymphocytes and T-cell lines.

TABLE 1

Origin and structure of T-cell growth factors

| FACTOR | SIZE (kDA) | NO. OF AMINO ACIDS* | SOURCE |
| --- | --- | --- | --- |
| IL-2 | 15 | 153 | Activated lymphocytes |
| IL-4 | 15–20 | 153 | Activated T-lymphocytes Bone marrow stromal cells Mast cells |
| IL-7 | 25 | 177 | Bone marrow and thymic stromal cells |
| IL-9 | 30–40 | 144 | Activated T-lymphocytes |
| IL-10 | 16–20 | 178 | Th2 lymphocytes |
| Il-12** | 40 and 35 | 328 and 253 | B-lymphoblastoid cell lines |
| ETF | 15–17 | 162 | Epithelial cells |

*Number in human polypeptides encoded by the open reading frame.
**Two glycoprotein subunits are necessary for activity.

"sET" refers to a simian species of ETF. "hETF" refers to a human species of ETF. "rETF" refers to recombinant ETF. Both purified sETF and rETF will stimulate proliferation of CTLL-2 cells (Gillis and Smithm *Nature* 268:154 (1977); ATCC TIB 214). In the CTLL-2 proliferation assays, supernatants of cells transfected with recombinantly expressed precursor and inframe fusions of mature forms of sETF induced CTLL-2 cell proliferation. For other assays, peripheral blood T-cells ("PBT") and peripheral blood mononuclear leukocytes ("PBL") were isolated from human peripheral blood. We found that rETF stimulated proliferation of PBT and PBL previously cultured with phytohemagglutinin ("PHA"). rETF also stimulated proliferation of PHA activated $CD4^+$ and $CD8^+$ cells. rETF stimulated proliferation of resting human T-cells or resting murine T-cell clones in the presence of anti-CD3 (T-cell receptor) antibodies.

Experiments with PHA activated PBT demonstrate that rETF exerts its growth stimulatory effects independently of IL-2, in that antibodies to IL-2 or to the IL-2 receptor do not inhibit ETF.

The terms ETF, sETF and hETF include analogs or subunits of native mammalian polypeptides that are encoded by nucleic acids that bind to the nucleic acid sequences in FIGS. 1 and 2 (nucleotides 145 through 489, inclusive, in SEQ ID NOS 1 and 4) under conditions of specified stringency and that induce proliferation and differentiation of T-lymphocytes, and stimulate proliferation of T-cell lines and isolated PBT.

"Recombinant DNA technology" or "recombinant", as used herein, refers to techniques and processes for producing specific polypeptides from microbial (e.g., bacterial, fungal or yeast) or mammalian cells or organisms (e.g., transgenics) that have been transformed or transfected with cloned or synthetic DNA sequences to enable biosynthesis of heterologous peptides. Native glycosylation patterns will only be achieved with mammalian cell expression systems. Yeast provide a distinctive glycosylation pattern. Prokaryotic cell expression (e.g., *E. coli*) will generally produce polypeptides without glycosylation.

"Biologically active" means that a particular mammalian ETF polypeptide is capable of stimulating T-lymphocyte proliferation and/or differentiation. In the case of sETF and hETF, this biological activity also corresponds to stimulation of the proliferation of murine or primate, for example, human, T-cell lines or PBT.

A "nucleotide sequence" refers to a polynucleotide in the form of a separate fragment or as a component of a larger DNA construct, that has been derived from DNA isolated at least once in substantially pure form (i.e., tree of contaminating endogenous materials) and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)) such as a cloning vector. Such sequences are preferably provided in the form of an open reading frame uninterrupted by internal nontranslated sequences, or introns, that are typically present in eukaryotic genes. Sequences of non-translated DNA may be present 5' or 3' from an open reading frame, where the same do not interfere with manipulation or expression of the coding regions.

"Recombinant expression vector" refers to a plasmid comprising a transcriptional unit comprising an assembly of (1) a genetic element or elements having a regulatory role in gene expression, for example, promoters or enhancers, (2) a structural or coding sequence that is transcribed into mRNA and translated into a polypeptide having ETF biological activity, and (3) appropriate transcription and translation initiation and termination sequences. The various regulatory elements that can be used are discussed below (see Recombinant DNA Techniques). Structural elements intended for use in yeast expression systems preferably include a leader sequence enabling extracellular secretion of translated polypeptide by a yeast host cell. Alternatively, in a bacterial expression system, the recombinant polypeptide may include a N-terminal methionine residue. The N-terminal methionine residue may be subsequently cleaved from the expressed recombinant polypeptide to provide a product suitable for further purification.

"Recombinant microbial expression system" refers to a substantially homogeneous monoculture of suitable host microorganisms, for example, bacteria, such as *E. coli*, or yeast, such as *S. cerevisiae*, that have stably integrated a recombinant transcriptional unit into chromosomal DNA or carry the recombinant transcriptional unit as a component of a resident plasmid. Generally, host cells constituting a recombinant microbial expression system are the progeny of a single ancestral transformed cell. Recombinant microbial expression systems will express heterologous polypeptides upon induction of the regulatory elements linked to a structural nucleotide sequence to be expressed.

Transformed host cells are cells that have been transformed or transfected with a recombinant expression vector. Expressed mammalian ETF will be located within the host cell and/or secreted into culture supernatant, depending upon the nature of the host cell and the gene construct inserted into the host cell.

Moderate stringency hybridization conditions, as defined herein and as known to those skilled in the art, refer to conditions described in, for example, Sambrook et al., supra, Vol. 2, pp. 8.46–8.49 and 9.47–9.55. Conditions of moderate stringency, as defined by Sambrook et al. include, for example, overnight hybridization and post-hybridization washes at 55° C., 5×SSC, 0.5% SDS. Severe or high stringency conditions include higher temperatures of hybridization and post-hybridization washes, or lower salt concentrations.

ETF Polypeptides

We have purified a simian species of ETF (sETF) and sequenced the N-terminal peptide of mature sETF. Using the N-terminal amino acid sequence and PCR, we isolated a cDNA encoding sETF and determined the nucleotide sequence and deduced amino acid sequence of mature sETF (FIG. 1), and the nucleotide sequence and deduced amino acid sequence of a precursor of sETF polypeptide (SEQ ID NO 1 and SEQ ID NO 2). Precursor ETF polypeptide sequence in the simian species comprises a mature active protein (SEQ ID NO 3) preceded by a 48-amino acid leader sequence. The leader sequence is MRISKPHLRS ISIQCYLCLL LKSHFLTEAG IHVFILGCFS AGLPKTEA amino acids 1–48 of SEQ ID NO 2. Primate ETF stimulates proliferation of murine T-cell lines (e.g., CTLL-2) and stimulates proliferation and differentiation of human PBT cells.

The present invention also comprises other mammalian ETF, including human ETF, having ETF biological activity and encoded by nucleotide sequences that hybridize, under conditions of moderate to high stringency, to probes defined by SEQ ID NO 4. A plasmid containing a recombinant clone of human ETF cDNA was deposited with the American Type Culture Collection ("ATCC") on Feb. 19, 1993 under accession number ATCC 69245. The deposit was named "I41-hETF" and comprised an *E. coli* strain containing plasmid hETF/pDC410 that contained a 31 6-bp 5' noncoding region preceding an open reading frame of 489 bp and a 397-bp 3' noncoding region flanked by the Sal I adaptors shown in SEQ ID NOS 7 and 8.

The amino acid structure of ETF polypeptides disclosed herein may be modified by forming covalent or aggregative conjugates with other chemical moieties, such as glycosyl groups, lipids, phosphate, acetyl groups and the like, or by creating amino acid sequence mutants. Covalent derivatives of mammalian ETF are prepared by linking particular functional groups to mammalian ETF amino acid side chains or at the N-terminus or C-terminus of a mammalian ETF polypeptide. Other derivatives of mammalian ETF within the scope of this invention include covalent or aggregative conjugates of mammalian ETF or its fragments with other proteins or polypeptides, such as by synthesis in recombinant culture as N-terminal or C-terminal fusions. For example, the conjugated polypeptide may be a signal (or leader) polypeptide sequence at the N-terminal region of a mammalian ETF polypeptide for transport from its site of synthesis to a site inside or outside of the cell membrane or wall (e.g., the yeast α-factor leader). Further, using conventional techniques, ETF polypeptides can be expressed as polypeptide fusions comprising additional polypeptide sequences, such as Fc or other immunoglobulin sequences, linker sequences, or other sequences that facilitate purification and identification of ETF polypeptides. Still further, ETF polypeptide fusions can comprise fusions with other cytokines to provide novel polyfunctional entities. Other cytokines include, for example, any of interleukins-1 through 13, tumor necrosis factor (TNF), granulocyte macrophage-colony stimulating factor (GM-CSF), granulocyte-colony stimulating factor (G-CSF), mast cell growth factor (MGF) and other cytokines that affect immune cell growth, dfferentiafion or function.

The present invention further includes ETF polypeptides having altered glycosylation. ETF polypeptides expressed in yeast or mammalian expression systems (e.g., COS-7 cells (ATCC CRL 1651)) may be similar or significantly different in molecular weight and glycosylation pattern than a native ETF polypeptide. This depends upon the choice of expression system. Expression of ETF polypeptides in bacterial expression systems, such as *E. coli*, provide non-glycosylated molecules.

Functional mutant analogs of human or other mammalian ETF can be synthesized, for example, with inactivated N-glycosylation sites by oligonucleotide synthesis and ligation or by site-specific mutagenesis techniques. ETF polypeptide derivatives can be expressed in homogeneous, reduced carbohydrate form using yeast expression systems. N-glycosylation sites in eukaryotic polypeptides are characterized by an amino acid triplet Asn-Φ-Ω where Φ is any amino acid except Pro and Ω is Ser or Thr. An ETF mutant derivative, as referred to herein, is a polypeptide substantially homologous to a sequence of a native mammalian ETF but that has an amino acid sequence different from a native mammalian ETF polypeptide because of a deletion, insertion or substitution.

Bioequivalent analogs of ETF polypeptides of ETF muteins may be constructed by making various substitutions of amino acid residues or sequences, or by deleting terminal or internal residues or sequences not needed for biological activity. For example, Cys residues can be deleted or replaced with other amino acids to prevent formation of incorrect intramolecular disulfide bridges upon renaturation. Other approaches to mutagenesis involve modification of dibasic amino acid residues to enhance expression in yeast systems in which KEX2 protease activity is present. Generally, substitutions are made conservatively by substituting an amino acid having physiochemical characteristics resembling those of the native residue.

Antisense or sense oligonucleotides comprise single-stranded nucleic acid sequences (either RNA or DNA) capable of binding to sense ETF mRNA or antisense ETF cDNA sequences. An antisense or sense oligonucleotide, according to the present invention, comprises a fragment of the nucleotide sequences in FIGS. 1 or 2 or a DNA or RNA complement of the nucleotide sequences in FIGS. 1 and 2. Such a fragment comprises at least about 14 nucleotides and is capable of binding to ETF DNA. The ability to create an antisense or a sense oligonucleotide, based upon a cDNA sequence for ETF is described in, for example, Stein and Cohen, *Cancer Res.* 48:2659 (1988), and van der Krol et al., *BioTechniques* 6:958 (1988).

Isolation and characterization of ETF from non-recombinant cellular sources requires a mammalian cell line that produces ETF and a responder cell line that proliferates in response to ETF stimulation. A biological assay for mammalian ETF may employ a growth factor-dependent T-cell line as a detector of factors that induce lymphoid cell proliferation. T-cells isolated from blood samples taken from humans or from other mammals also can be used to assay mammalian ETF polypeptides.

An ETF-dependent cell line can be derived from murine CTLL-2 cells. This cell line responds to purified human, murine, and recombinant IL-2 and murine IL-4 but not to IL-1, IL-3, human IL,-4, or any of the other known growth factors.

One can utilize the simian or human ETF cDNA sequences disclosed herein to obtain cDNAs encoding other mammalian homologs of simian or human ETF by cross-species hybridization techniques. Briefly, an oligonucleotide probe is created from the nucleotide sequence of the protein coding region of sETF cDNA as described in FIG. 1 or SEQ ID NO 1 or hETF cDNA as described in FIG. 2 or SEQ ID NO 4. This probe can be made by standard techniques, such as those described in Sambrook et al. supra. The simian or human probe is used to screen a mammalian cDNA library or genomic DNA library under moderate stringency conditions. Mammalian cDNA libraries can be made from mRNAs isolated from, for example, murine peripheral blood lymphocytes. Alternatively, other cDNA libraries or mRNAs isolated from various tissues or cell lines can be screened by Northern hybridization to determine a suitable source of mammalian ETF DNA or mRNA.

CV-1/EBNA ETF Purification

We have purified ETF to provide an isolated polypeptide preparation from a non-homogeneous protein solution, such as conditioned medium collected from cells expressing ETF. ETF activity in crude conditioned medium samples is not always detectable using currently available ETF bioassay techniques. At least one purification step is typically required before ETF biological activity is detectable utilizing bioassay techniques described herein.

A non-homogeneous protein solution, e.g., conditioned medium, is prepared by growing the CV-1/EBNA line (C. J. McMahan et al., *EMBO J.*, 10(10):2821–2832 (1991); ATCC CRL 10478) of African Green Monkey kidney cells in a tissue culture medium. Preferably, the medium is high glucose Dulbecco's Modified Essential Medium ("DMEM", Gibco). Most preferably, a growth medium and a production medium are used. The growth medium employed in isolating sETF as described herein was high glucose (4500 rag/L) DMEM supplemented with 7.5% fetal bovine serum. 50 u/ml penicillin, 50 ug/ml streptomycin, 3 to 4.0 mM L-glutamine. 1 mM sodium pyruvate, 0.1 mM non-essential amino acids and 10 mM N-[2-hydroxyethyl]piperazine-N'-[2-ethanesulfonic acid] ("HEPES") buffer. A serum free production medium of DMEM without phenol red supplemented with 50 u/ml penicillin, 50 ug/ml streptomycin, 3 to 4.0 mM l,-glutamine, 1 mM sodium pyruvate, 0.1 mM non-essential amino acids and 10 mM HEPES buffer was developed for ETF production and purification. The CV-1/EBNA cells were attachment dependent and could be grown in dishes, flasks, roller bottles or microcarriers.

More specifically, ETF was produced by culturing CV-1/EBNA cells on microcarriers in a controlled bioreactor. Cell stocks were maintained in roller bottle flasks. To start a production cycle, cells were trypsinized and inoculated into a spinner flask containing the growth medium described above and 5 g/l Cytodex® 3 microcarriers (Pharmacia). Initial seeding density ranged from 1.5 to 3.5×10$^5$ cells/ml. To ensure efficient cell attachment to the microcarriers, the cells were kept in the spinner flask for 2 to 24 hours. Spinner flask cultures were incubated at 37° C. and agitated at 25 to 40 RPM. After the attachment period, the culture was transferred to a controlled bioreactor. Bioreactor temperature, pH, oxygen and agitation set points were 37° C., 7.0, 20% saturation (relative to air), and 75–85 RPM, respectively. For routine observation of cell growth and health, samples were observed by bright field microscopy. Quantification of cell growth was achieved by counting released nuclei after treatment with a solution of 100 mM citric acid and 0.1% crystal violet.

The culture was supplemented with additional growth medium when ammonia levels reached 5.0 mM. This was repeated until the microcarriers were confluent. The culture medium was then exchanged to the serum-free production medium described above. This procedure was accomplished by allowing the microcarriers to settle to the bottom of the reactor, aspirating the growth medium and replacing it with production medium. This was repeated until an approximately 3,125 fold dilution was achieved. Two to six rounds of production can be expected. In each round, cells were allowed to produce for four to seven days after which 80% of the production medium was collected. This was repeated until the cells were completely detached from the microcarriers.

Approximately 64 liters of CV-1/EBNA conditioned media were used to purify and provide protein for the N-amino acid sequence of sETF. As shown in FIG. 3, the purification scheme included ultrafiltration, hydrophobic chromatography, anion exchange chromatography, reverse phase high performance liquid chromatography (RP-HPLC), and sodium dodecyl sulfate polyacrylamide gel electrophoresis (SDS-PAGE). Protein was sequenced by blotting the SDS gel to a polyvinylidene fluoride ("PVDF") membrane and determining an N-terminal amino acid sequence by Edman degradation directly from the PVDF membrane. N-terminal amino acid sequencing revealed the first 33 amino acids shown in SEQ ID NO 3. Subsequent sequencing of a cDNA clone obtained from a CV-1/EBNA cDNA library produced a DNA sequence encoding the polypeptide of SEQ ID NO 2. This clone includes a relatively short 48 amino acid leader sequence from SEQ ID NO 2 and a mature polypeptide represented by SEQ ID NO 3.

Recombinant DNA Techniques

Human, simian and other mammalian ETF polypeptides are preferably produced by recombinant DNA techniques. Such techniques involve insertion of a cDNA encoding a human or other mammalian ETF polypeptide or a derivative thereof into an expression vector.

Recombinant production of mammalian ETF polypeptides or derivatives thereof first requires isolation of a DNA clone (i.e., cDNA) that codes on expression for a mammalian ETF polypeptide or a derivative thereof. cDNA clones are derived from primary cells or cell lines that express mammalian ETF polypeptides. First total cell mRNA is isolated, then a cDNA library is made from the mRNA by reverse transcription. A cDNA clone may be isolated and identified using the DNA sequence information provided herein to design a cross-species hybridization probe or PCR primer as described below.

The isolated cDNA is preferably in the form of an open reading frame uninterrupted by internal nontranslated sequences, or introns. Genomic DNA containing the relevant nucleotide sequences that code for expression of mammalian ETF polypeptides can also be used as a source of genetic information useful in constructing coding sequences. The isolated cDNA can be mutated by techniques known in the an to promote ETF derivatives or analogs that exhibit ETF biological activity.

Recombinant expression vectors include synthetic or cDNA-derived DNA fragments encoding ETF or biologically active derivatives thereof. The DNA encoding a ETF or a derivative thereof is operably linked to a suitable transcriptional or translational regulatory or structural nucleotide sequence, such as one derived from mammalian, microbial, viral or insect genes. Examples of regulatory sequences include, for example, a genetic sequence having a regulatory role in gene expression (e.g., transcriptional promoters or enhancers), an optional operator sequence to control transcription, a sequence encoding suitable mRNA ribosomal binding sites, and appropriate sequences that control transcription and translation initiation and termination. Nucleotide sequences are operably linked when the regulatory sequence functionally relates to the structural gene. For example, a DNA sequence for a signal peptide (secretory leader) may be operably linked to a structural gene DNA sequence for a mammalian ETF or derivative thereof if the signal peptide is expressed as part of a precursor amino acid sequence and participates in the secretion of a mammalian ETF. Further, a promoter nucleotide sequence is operably linked to a coding sequence (e.g., structural gene DNA) if the promoter nucleotide sequence controls the transcription of the structural gene nucleotide sequence. Still further, a ribosome binding site may be operably linked to a structural gene nucleotide coding sequence (e.g., mammalian ETF) if the ribosome binding site is positioned within the vector to encourage translation.

Suitable host cells for expression of mammalian ETF or derivatives thereof include prokaryotes, yeast or higher eukaryotic cells under the control of appropriate promoters. Prokaryotes include gram negative or gram positive organisms, for example *E. coli* or bacilli. Suitable prokaryotic hosts cells for transformation include, for example, *E. coli, Bacillus subtilis, Salmonella typhimurium*, and various other species within the genera *Pseudomonas, Streptomyces,* and *Staphylococcus*. As discussed in greater detail below, examples of suitable host cells also include yeast such as *S. cerevisiae,* a mammalian cell line such as Chinese Hamster Ovary (CHO) cells, or insect cells. Cell-free translation systems could also be employed to produce mammalian ETF or derivatives thereof using RNAs derived from the DNA constructs disclosed herein. Appropriate cloning and expression vectors for use with bacterial, fungal, yeast, and mammalian cellular hosts are described, for example, in Pouwels et al. *Cloning Vectors: A Laboratory Manual,* Elsevier, N.Y., 1985.

When a mammalian ETF or derivative thereof is expressed in a yeast host cell, the nucleotide sequence (e.g., structural gene) that codes on expression for a mammalian ETF or derivative thereof may include a leader sequence. The leader sequence may enable improved extracellular secretion of translated polypeptide by a yeast host cell.

Mammalian ETF may be expressed in yeast host cells, preferably from the Saccharomyces genus (e.g., *S. cerevisiae*). Other genera of yeast, such as Pichia or Kluyveromyces, may also be employed. Yeast vectors will often contain an origin of replication sequence from a 2 µ yeast plasmid, an autonomously replicating sequence (ARS), a promoter region, sequences for polyadenylation, and sequences for transcription termination. Preferably, yeast vectors include an origin of replication sequence and selectable marker. Suitable promoter sequences for yeast vectors include promoters for metallothionein, 3-phosphoglycerate kinase (Hitzeman et al., *J. Biol. Chem.* 255:2073, 1980) or other glycolytic enzymes (Hess et al *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EP-A-73,657.

Yeast vectors can be assemble& for example, using DNA sequences from pBR322 for selection and replication in *E. coli* (Amp$^r$ gene and origin of replication). Other yeast DNA sequences that can be included in a yeast expression construct include a glucose-repressible ADH2 promoter and or-factor secretion leader. The ADH2 promoter has been described by Russell et al. (*J. Biol. Chem.* 258:2674, 1982) and Beier et al. (*Nature* 300:724, 1982). The yeast α-factor leader sequence directs secretion of heterologous polypeptides. The α-factor leader sequence is often inserted between the promoter sequence and the structural gene sequence. See, e.g., Kurjan et al., *Cell* 30:933, 1982; and Bitter et al., *Proc. Natl. Acad. Sci. USA* 81:5330, 1984. A leader sequence may be modified near its 3' end to contain one or more restriction sites. This will facilitate fusion of the leader sequence to the structural gene.

Yeast transformation protocols are known to those skilled in the an. One such protocol is described by Hinnen et al., *Proc. Natl. Acad. Sci. USA* 75: 1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Alternatively, in a prokaryotic host cell, such as *E. coli,* the mammalian ETF or derivative thereof may include an N-terminal methionine residue to facilitate expression of the recombinant polypeptide in a prokaryotic host cell. The N-terminal Met may be cleaved from the expressed recombinant mammalian ETF.

The recombinant expression vectors carrying the recombinant mammalian ETF structural gene nucleotide sequence or derivative thereof are transfected or transformed into a suitable host microorganism or mammalian cell line.

Expression vectors transfected into prokaryotic host cells generally comprise one or more phenotypic selectable markers. A phenotypic selectable marker is, for example, a gene encoding proteins that confer antibiotic resistance or that supply an autotrophic requirement, and an origin of replication recognized by the host to ensure amplification within the host. Other useful expression vectors for prokaryotic host cells include a selectable marker of bacterial origin derived from commercially available plasmids. This selectable marker can comprise genetic elements of the cloning vector pBR322 (ATCC 37017). pBR322 contains genes for ampicillin and tetracycline resistance and thus provides simple means for identifying transformed cells. The pBR322 "backbone" sections are combined with an appropriate promoter and a mammalian ETF structural gene sequence. Other commercially available vectors include, for example, pKK223-3 (Pharmacia Fine Chemicals, Uppsala, Sweden) and pGEM1 (Promega Biotec, Madison, Wis., USA).

Promoter sequences are commonly used for recombinant prokaryotic host cell expression vectors. Common promoter sequences include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EPA 36,776) and tac promoter (Sambrook et al., *Molecular Cloning: A Laboratory Manual,* Cold Spring Harbor Laboratory, (1989)). A particularly useful prokaryotic host cell expression system employs a phage $\lambda$ $P_L$ promoter and a cI857ts thermolabile repressor sequence. Plasmid vectors available from the American Type Culture Collection that incorporate derivatives of the $\lambda$ $P_L$ promoter include plasmid pHUB2 (resident in *E. coli* strain JMB9 (ATCC 37092)) and pPLc28 (resident in *E. coli* RR1 (ATCC 53082)).

Mammalian or insect host cell culture systems also could be employed to express recombinant mammalian ETF polypeptide or derivatives thereof. Examples of suitable mammalian host cell lines include the COS-7 lines of monkey kidney cells (Gluzman et al., *Cell* 123:175, (1981);ATCCCRL 1651),L cells, C127 cells, 3T3cells(ATCCCCL 163), CHO cells, HeLa cells (ATCC CCL 2), and BHK (ATCC CRL 10) cell lines. Suitable mammalian expression vectors include nontranscribed elements such as an origin of replication, a promoter sequence, an enhancer linked to the structural gene, other 5' or 3' flanking nontranscribed sequences, such as ribosome binding sites, a polyadenylation site, splice donor and acceptor sites, and transcriptional termination sequences.

Transcriptional and translational control sequences in mammalian host cell expression vectors may be provided by viral sources. For example, commonly used mammalian cell promoter sequences and enhancer sequences are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a structural gene sequence in a mammalian host cell. Vital early and late promoters are particularly useful because both are easily obtained from a viral genome as a fragment that may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary mammalian expression vectors can be constructed as disclosed by Okayama and Berg (*Mol. Cell. Biol.* 3:280, 1983). Additional useful mammalian expression vectors are described in U.S. patent application Ser. No. 07/480,694 filed Feb. 14, 1990 and U.S. patent application Ser. No. 07/543,193 filed Jun. 5, 1990.

Purification of Recombinant Mammalian ETF

ETF polypeptides may be prepared by culturing transformed host cells under culture conditions necessary to express mammalian ETF polypeptides or derivatives thereof. The resulting expressed polypeptides may then be purified from culture media or cell extracts. A mammalian ETF polypeptide or derivative thereof may be concentrated using a commercially available protein concentration filter, for example, an Areicon or Millipore Pellicon ultrafiltration unit. With or without the concentration step, the culture media can be applied to a purification matrix such as a hydrophobic chromatography medium. Phenyl Sepharose® CL-4B (Pharmacia) is the preferred medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, gel filtration medium can be used. Recombinant ETF is stable in acidic aqueous buffers and a cation exchange resin also can be used.

Finally, one or more reverse-phase high performance liquid chromatography (RP-HPLC) steps employing hydrophobic RP-HPLC media, e.g., silica gel having pendant methyl or other aliphatic groups, can be employed to further purify ETF. Some or all of the foregoing purification steps, in various combinations, can also be employed to provide a substantially homogeneous recombinant protein. Alternatively, some or all of the steps used in the purification procedure described above for simian ETF can also be employed.

Recombinant protein produced in bacterial culture is usually isolated by initial disruption of the host cells, centrifugation, extraction from cell pellets if an insoluble polypeptide, or from the supernatant if a soluble polypeptide, followed by one or more concentration, salting-out, ion exchange or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express ETF as a secreted polypeptide. This simplifies purification. Secreted recombinant polypeptide from a yeast host cell fermentation can be purified by methods analogous to those disclosed by Urdal et al. (*J. Chromatog.* 296: 171, 1984). Urdal et al. describe two sequential, reversed-phase HPLC steps for purification of recombinant human IL-2 on a preparative HPLC column.

Administration of Mammalian ETF Polypeptide and Derivative Compositions

The present invention provides methods of using therapeutic compositions comprising an effective amount of ETF in a suitable diluent or carrier. For therapeutic use, purified ETF or a biologically active derivative thereof is administered to a patient, preferably a human, for treatment in a manner appropriate to the indication. Thus, for example, ETF compositions administered to suppress a form of anemia can be given by bolus injection, continuous infusion, sustained release from implants, or other suitable technique. Typically, an ETF therapeutic agent will be administered in the form of a pharmaceutical composition comprising purified polypeptide in conjunction with physiologically acceptable carriers, excipients or diluents. Such carriers will be nontoxic to patients at the dosages and concentrations employed. Ordinarily, the preparation of such compositions entails combining a mammalian ETF polypeptide or derivative thereof with buffers, antioxidants such as ascorbic acid, low molecular weight (less than about 10 residues) polypeptides, proteins, amino acids, carbohydrates including glucose, sucrose or dextrans, chelating agents such as EDTA, glutathione and other stabilizers and excipients. Neutral buffered saline or saline mixed with conspecific serum albumin are exemplary appropriate diluents.

The following examples are for purposes of illustration and not by way of limitation.

EXAMPLE 1

PURIFICATION AND SEQUENCING FOR NATIVE sETF

Ultrafiltration

Ultrafiltration was not absolutely necessary to purify ETF. The procedure, however, does remove certain smaller contaminating proteins and reduces the volume, thus speeding up the purification scheme. The ultrafiltration step can be performed using either a YM10 or YM30 spiral cartridge, a hollow fiber cartridge, or a disc membrane in various types of ultrafiltration apparatus. An Areicon ultrafiltration system with a YM30 spiral cartridge, however, was preferred. No buffer exchange was required before or after this step.

A non-homogeneous protein solution, i.e. conditioned medium was obtained by growing CV-1/EBNA cell cultures in serum free, phenol red free DMEM in bioreactors with 5 g/l Cytodex® 3 microcarriers. 8×8 liter bioreactors (total of about 64 liters) were harvested, centrifuged to remove cells and microcarriers, filtered through a 0.22 micron cellulose acetate membrane filter, and then concentrated to a final volume of about two liters using a YM30 spiral cartridge. Preferably, the YM30 concentrate is filtered before undergoing hydrophobic chromatography. This step will minimize contamination by removing bacteria and other particulates. Any filter having a pore size from 0.1 to 0.45 microns that does not bind protein may be used: however, a 0.22 micron cellulose acetate membrane filter was preferred.

Hydrophobic Chromatography

Hydrophobic chromatography provided a quick way of transferring the protein into a low salt buffer that could be applied to anion exchange columns. In addition, it provided three to six fold purification. Still further, no buffer exchange was required before or after this step. Various hydrophobic columns are suitable. A Phenyl Sepharose® CL-4B column (Pharmacia) was preferred. As an alternative to the hydrophobic chromatography step described herein, a diafiltration or dialysis step can be used.

Preferably, ammonium sulfate was added to the ultrafiltration concentrate to a final concentration of about 0.2 M. The ultrafiltration concentrate was buffered with 1 M HEPES at about pH 8.5 to a final concentration of about 20 mM. The concentrate was then pumped onto a Phenyl Sepharose® CL-4B column and washed with 0.2 M ammonium sulfate 10 mM HEPES at about pH 8.5 to remove unbound protein. Bound proteins were eluted with 10 mM HEPES at about pH 8.5. The eluted protein peak (including ETF) was applied to an anion exchange column.

Anion Exchange Chromatography

Anion exchange chromatography purification allowed additional purification without requiring dialysis or buffer exchange. This step preferably involved two passages of the Phenyl Sepharose® protein pool over columns containing an anion exchange media. After each passage, the bound proteins were eluted with NaCl in HEPES. Although various anion exchange media and buffer systems having a pH of about 8 to about 9 were suitable, DEAE Sephacel® (Pharmacia) followed by Mono Q allowed sequential anion exchange steps without buffer exchanges or dialysis. DEAE Sephacel® provided removal of some contaminating proteins prior to application to a higher resolution Mono Q fast performance liquid chromatography ("FPLC," Pharmacia). The NaCl concentration used depended on the anion exchanger selected and the pH of the buffer chosen. Other salts could be substituted for the NaCl to elute the protein from the anion exchange gel.

Most preferably, NaCl was added to the Phenyl Sepharose pool to a final conductivity of about 1.2 milliSiemens/Centimeter ("mS/cm") (less than approximately 0.1 M NaCl) and pumped onto a DEAE Sephacel® column that was equilibrated with about 0.1M NaCl in about 10 mM HEPES at about pH 8.5. Bound proteins were eluted with a linear gradient from about 0.1 to about 0.3 M NaCl in about 10 mM HEPES at about pH 8.5. The protein active fractions eluted (including ETF) were pooled for application to a Mono Q anion exchange column.

The active DEAE Sephacel(g) pool was diluted with about 10 mM HEPES to a final conductivity less than 1.6 mS/cm (less than 0.14 M NaCl). The diluted pool was then pumped onto a Mono Q FPLC fast performance liquid chromatography column that was equilibrated with about 0.14 M NaCl in about 10 mM HEPES at about pH 8.5. Bound proteins were eluted with a gradient from about 0.14 M to about 0.5 M NaCl in about 10 mM HEPES at about pH 8.5. The active fractions (including ETF) were pooled for application to reverse phase high performance liquid chromatography (RP-HPLC).

RP-HPLC

The native mammalian ETF polypeptide is stable from approximately pH 7 to approximately 9 and at approximately pH 2.5 in 0.1% trifluoroacetic acid ("TFA"), in acetonitrile ("AcN"). The ETF activity was not recovered when acidic aqueous buffers were used; thus eliminating many HPLC buffer systems and not allowing cation exchange chromatography to be included in the purification scheme. C4 RP-HPLC columns (Vydac™ 0.46×25 cm, 5 micron) provided the greatest purification. Other reverse phase columns (C8 or C18) did not work: the protein eluted from C4 at a high AcN concentration and was not recovered from C8 or C 18 at all. Other buffer systems that we tried (i.e., ammonium acetate/methanol pH 7 and pyridine acetate/propanol) were not successful.

The RP-HPLC purification preferably involved two passages of the Mono Q active pool over the Vydac™ C4 matrix. In the first passage, the Mono Q active pool was pumped onto a C4 HPLC column at about 1 ml/min and eluted with a gradient of 0.1% TFA/$H_2O$ to 0.1% TFA/100% AcN at the following gradient:

0 to 45% AcN. 1% AcN/minute 45 to 60% AcN, 0.5% AcN/minute 60 to 100% AcN, 2% AcN/minute Peak active fractions (including ETF) elute between about 48 and about 51% AcN. Active fractions determined by bioassay were pooled, diluted with 0.1% TFA/H$_2$O to reduce AcN concentration, and applied to the same C4 column.

The active, diluted pool from the C4 TFA/AcN run was pumped back on to the C4 column, washed with 0.1% TFA/H20 and eluted with a linear gradient of 0.1% TFA/H$_2$O (buffer A) to 0.1% TFA/60% n-propanol (buffer B) at about 0.5 ml/min. The gradient was run at about 0.5% buffer B/min. Fractions were bioassayed to identify the ETF-containing fractions. ETF-containing fractions were pooled.

SDS-PAGE

Purified ETF can be visualized by silver stained SDS-PAGE. Purified mammalian ETF protein bands isolated by SDS-PAGE may be electroblotted and analyzed to determine their N-terminal amino acid sequences. The ETF protein band can be identified by bioassay.

Purified ETF protein fractions from the C4 TFA/n-propanol HPLC run were speed vacuumed to dryness, resuspended in reducing SDS sample buffer and run on a polyacrylamine SDS gel. Preferably, HPLC purified ETF was run on SDS-PAGE (Phastgel® 8-25%, Pharmacia) in two adjacent lanes. Prior to fixing and staining, approximately 1 mm slices of gel were cut from one lane of the Phastgel® and put directly into bioassays. The remaining gel was developed and the silver stained bands matched with slices put into bioassays. The ETF activity corresponded to 15-17 kDa. For specific activity determination, purified ETF was resuspended in reducing SDS sample buffer, run on 14% polyacrylamide SDS gel (Novex) and silver stained. The purity of the sETF polypeptides corresponding to 15-17 kDa was approximately 222,000 times greater than the sETF polypeptide purity in the CV-1/EBNA conditioned media at the beginning of the purification scheme (Table 2).

PVDF Blot

The 14% polyacrylamide SDS gel was blotted to a PVDF membrane (ProBlot® from Applied Biosystems) using constant current, at about a 60 V setting for about one hour. Protein bands were visualized by staining the PVDF membrane with Coomassie blue (0.1% in 10% acetic acid, 50% methanol). The membrane may be destained using the same solution without the Coomassie blue stain to highlight the protein bands. The protein band corresponding to the ETF activity was cut out and N-terminal protein sequence determination was performed directly from the PVDF membrane.

sETF Polypeptide Sequencing

The ETF preparation resulting from the foregoing RP-HPLC step was analyzed by SDS-PAGE. Each gel was silver stained to indicated the presence of protein bands. Bioassay of unstained gel slices corresponding to visible bands indicated the ETF activity was associated with proteins having molecular weights in the range of 15–17 kDa. The N-terminus of the 15–17 kDa polypeptide, blotted onto a PVDF membrane, was sequenced by Edman degradation in an Applied Biosystems protein sequencer. The results indicated the identity of the first 33

TABLE 2

| SAMPLE | VOLUME | PROTEIN CONC. UG/ML | TOTAL PROTEIN | ACTIVITY UNITS/ML[2] | TOTAL ACTIVITY UNITS | SPECIFIC ACTIVITY UNITS/UG | FOLD PURIFICATION |
|---|---|---|---|---|---|---|---|
| Crude | 64 L | 40–70 | 3.2 g | <100 | | (1.0) | 1 |
| Phenyl Seph SM | 1.7 L | 2100 | 3.6 g | 3000 | 5,100,000 | 1.4 | 1.4 |
| DEAE SM | 364 ml | 1300 | 473 mg | 5100 | 1,900,000 | 3.9 | 3.9 |
| Mono Q SM | 215 ml | 310 | 66.65 mg | 7664 | 1,650,000 | 24.8 | 25 |
| HPLC TFA-AcN SM | 14 ml | ND[3] | ND | 70546 | 987,644 | ND | ND |
| HPLC TFA-prop SM | 4 ml | ND | ND | 220,000 | 880,000 | ND | ND |
| TFA-prop peak | 2 ml | (88) | (176 ug) | 440,000 | 888,000 | (5045) | (5000) |
| SDS PAGE band | | | (4 ug) | | | (222,000) | (222,000) |

Monkey ETF from CV-L/EBNA cell-conditioned serum free media[1]

[1]Values in parenthesis are estimates from silver stained SDS PAGE. Other protein values were determined by Biorad Microprotein Assay (BSA standard)
[2]Activity was determined by CTLL-2 bioassay
[3]ND = not determined amino acids shown in SEQ ID NO 3. Subsequent sequencing of a cDNA clone obtained from a simian library provided a sequence encoding the polypeptide of SEQ D NO 2. The polypeptide of SEQ ID NO 2 comprises a relatively short 48 amino acid leader sequence and a mature polypeptide represented by SEQ ID NO 3.

EXAMPLE 2

BIOASSAY

CTLL-2 cells provide a fast and sensitive bioassay for detection of ETF polypeptides. Other cell lines that also proliferate in response to ETF with varying sensitivity are CTLL-2.4 (Valentine et al., *Eur J. Immunol.*, 21(4):913 (1991)) 32D, (Greenberger, *Federation Proceedings* 42:2762 (1983)), BAF-BO3 (Hatakeyama et al., *Cell*, 59:837 (1989)), MO7e (Avanzi et al., *Br. J. Haematol.* 69:359 (1988)), and TF1 (Kitamura et al., *J. Cell. Physciol.*, 140:323 (1989)).

Preferably, CTLL-2 cells were grown in high glucose DMEM supplemented with about 30 ng/ml IL-2, 5% fetal bovine serum (FBS), 5×10$^{-5}$ M 2-mercaptoethanol, 50 u/ml penicillin, 50 ug/ml streptomycin, and 3–4.0 mM L-glutamine at 37° C., 10% CO$_2$ and 97% humidity. CTLL-2 is a factor dependent cell line requiring IL-2 for growth. Consequently, for assay, CTLL-2 cells were washed twice with high glucose DMEM supplemented with 5% FBS, 5×10⁻⁵ M 2-mercaptoethanol, 50 u/ml penicillin, 50 ug/ml streptomycin, 3–4.0 mM L-glutamine to remove IL-2. ETF samples to be assayed were titrated in DMEM 5% FBS in 96 well flat-bottomed microliter plates. Washed CTLL-2 cells were added (final assay volume 100 μl 2000 cells/well) and the plates incubated about 24 hours at 37° C. and 10% $CO_2$. The plates were pulsed with ³H-thymidine (25Ci/mMole) at 0.5 μCi/well for about 5 hours, then harvested (Inotech 96 well cell harvester) and CPM counted (Packard Matrix 96 gas proportional counting system). Units were calculated from CPM where 1 unit equals the number of microliters that gives 50% maximal stimulation.

EXAMPLE 3

PREPARATION OF sETF eDNA CLONE

The sequence of the N-terminal 31 amino acids of purified sETF polypeptide (amino acids 1–31 in SEQ ID NO 3) was used to design synthetic oligonucleotide primers for PCR amplification of ETF-specific DNA sequences. The first six antino acids of the N-terminus (Asn-Trp-Val-Asn-Val-Ile) were used to design one primer, a degenerate mixture coding for all possible codon usages of the first six amino acid residues:

5'-AAYTGGGTNAAYGTNATH-3' as shown in SEQ ID NO 9 where Y is T or C; H is A, T, or C; and N is A, C, G, or T. The amino acid sequences of the simian mature N-terminus 26–31 (Tyr-Thr-Glu-Ser-Asp-Val) were used to design a second primer, a degenerate mixture coding for a complement of all possible codon usages of amino acids 26–31 omitting position 3 of Val:

5'-TCGACTGGAACGAGACGACCTGCT-3'

3'-GACCTTGCTCTGCTGGACGA-5' as shown in SEQ ID NOS 10 and 11, respectively, where Y and N are as defined above and R is A or G.

Polyadenylated RNAs from CV-1/EBNA cells stimulated for 24 hr, 37 hr, and 72 hr with 10 ng/ml phorbol 12myristate 13-acetate ("PMA") were used as separate templates for first strand cDNA synthesis. A portion of first strand reactions was added to commercially available PCR reaction mixes containing the oligonucleotide primers. This mixture was subjected to 31 cycles of PCR amplification in 100 μl reactions in standard buffer with the primers at 1 μM concentration. The cycles were programmed as follows: denaturation at 94° C. for 0.5 min., annealing step for 0.5 rain, and elongation step at 72° C. for 0.75 min. Two cycles of annealing at each of 55° C., 53° C., and 51° C. were followed by 25 cycles with an annealing temperature of 49° C.

Following amplification, samples were purified and subjected to agarose gel electrophoresis. This yielded a 92 base pair DNA fragment that was excised from gel lanes from two separate reactions involving CV-1/EBNA cells. The 92 base pair DNA fragment was purified using an Elutip-D column (Schleicher & Schuell, Keene N.H.), cloned into pBluescript SK- (Stratagene. La Jolla, Calif.) and used for dideoxy DNA sequencing.

A hybridization probe was prepared by random prime labeling of the subcloned 92 base pair DNA fragment. The hybridization probe was used to screen a portion of a plasmid library containing cDNA inserts prepared from CV-1/EBNA polyadenylated RNA. This resulted in the isolation of clone C85.sETF that has an open reading frame comprising the nucleotide sequence shown in SEQ ID NO 1.

The nucleotide sequence of the polypeptide coding region of sETF is illustrated in SEQ ID NO 1. This sequence was derived from insert C85.sETF that was Sal I linkered into the Sal I site of expression vector pDC406 (C. J. McMahan et al., *EMBO J.*, 10(10):2821–2832 (1991)). Polyadenylated mRNA was prepared from a CV-1/EBNA cell line and cDNAs were prepared using standard techniques. The CV-1/EBNA line is a producer of sETF. cDNA ends were adapted with Sal I adapters (Haymerle et al., *Nucleic Acid Res*, 14:8615–24 (1986)):

5'-ACRTCNGAYTCNGTRTA-3' and

5'-ACRTCRCTYTCNGTRTA-3'

(SEQ ID NOS 7 and 8, respectively) and cloned into vector pDC406. A pool consisting of approximately 500 individual plasmid-containing isolates was plated and screened by hybridization to a DNA probe fragment. The DNA probe fragment was prepared using PCR amplification of sETF sequences from CV-1/EBNA cell line cDNA.

EXAMPLE 4

CLONING HUMAN ETF

A sETF probe was prepared from an isolated, purified and radiolabeled SaI I fragment (about 1.37 kb) containing sETF eDNA by random prime labeling. The specific activity of the probe was approximately $1\times10^6$ cpm/ng. On Northern blots, the probe was hybridized to human RNAs from various sources, including a IMTLH cell line. The IMTLH cell line was derived from a stable transformation of a human bone marrow stromal cell culture with pSV3Neo. The probe was hybridized to human RNAs at about 42° C. in about 40% formamide for about 18 hours. Hybridization was followed by washing in 6×SSC for about ten minutes at 22° C. followed by washing in 2×SSC at 42° C. for about 30 minutes. Autoradiography revealed a positive signal in the IMTLH lane.

We probed Southern blots of Sal I-digested library pools of the IMTLH cDNA library to identify a pool containing a human ETF cDNA. Using the Haymerle et al., *Nucleic Acid Res*, 14:8615–24 (1986) method used above for the CV-1/EBNA library, the IMTLH library was constructed in expression vector pDC410, a derivative of pDC406 that has additional restriction sites at the multiple cloning site, an additional downstream T7 polymerase binding site, and a SV40 large T antigen substituted for the EBV origin of replication. Pool "I41", a pool of approximately 1000 different eDNA clones, was identified as positive. Approximately 4000 colonies of "I41" then were plated and probed by conventional colony hybridization methods to identify a clone containing the human ETF cDNA. Only a single clone, I41 .hETF, was shown to encode human ETF. There is approximately 96% nucleotide sequence identity and approximately 96% amino acid sequence identity between human and simian ETF open reading frame sequences (FIGS. 4 and 5).

EXAMPLE 5 rETF STIMULATION OF CTLL-2 PROLIFERATION cDNAs encoding mature forms of ETF (nucleotides 145 to 489, inclusive, in SEQ ID NOS 1 and 4) were inserted downstream of a heterologous mammalian secretion signal to create rETF expression plasmid for sETF and hETF. The secretion signal is a largely hydrophobic stretch of amino acids (usually at the N-terminus of a polypeptide) that directs secretion and cleavage of the polypeptide between the C-terminus of the signal peptide and the N-terminus of the mature secreted protein (yon Heijne, *Eur. J. Biochem.*, 116:419 (1981)). The secretion signal sequence used was a murine IL-7 signal sequence. The created plasmids were transfected into COS-7 cells. Supernatants of the transfected cell cultures stimulated CTLL-2 proliferation. In addition, the coding region for the precursor form of hETF (SEQ ID NO 3) was inserted into pDC406 and transfected into CV-1/EBNA cells. Supernatants from cells transfected with pDC406:hETF, but not those transfected with empty vector, stimulated CTLL-2 proliferation.

---

What is claimed is:

1. An isolated DNA sequence encoding a mammalian epithelium-derived T-cell factor (ETF) polypeptide, wherein the DNA sequence is selected from the group consisting of:

(a) a DNA sequence encoding a mammalian ETF polypeptide comprising (SEQ. ID NO 12):

Asn Trp Val Asn Val Ile Ser Asp Leu Lys Lys Ile Glu Asp Leu
1           5                    10                   15

Ile Gln Ser Met His Ile Asp Ala Thr Leu Tyr Thr Glu Ser Asp
        20                    25                    30

Val His Pro Ser Cys Lys Val Thr Ala Met Lys Cys Phe Leu Leu
          35                    40                    45

Glu Leu Gln Val Ile Ser Xaa Glu Ser Gly Asp Xaa Xaa Ile His
              50                    55                    60

Asp Thr Val Glu Asn Leu Ile Ile Leu Ala Asn Asn Xaa Leu Ser
              65                    70                    75

Ser Asn Gly Asn Xaa Thr Glu Ser Gly Cys Lys Glu Cys Gly Glu
              80                    85                    90

Leu Glu Glu Lys Asn Ile Lys Glu Phe Leu Gln Ser Phe Val His
              95                    100                   105

Ile Val Gln Met Phe Ile Ans Thr Ser
                  110 wherein amino acid 52 is Leu or His, amino acid 57 is Ala or Thr, amino acid 58 is Ser or Asp, amino acid 73 is Ser or Ile, and amino acid 80 is Val or Ile; and (b) DNA sequences that detectably hybridize to the DNA sequences of (a) or their complementary strands under conditions of high stringency and upon expression encode mammalian ETF.

2. An isolated DNA sequence according to claim 1, wherein said DNA sequence encoding a mammalian ETF polypeptide comprises a DNA sequence selected from the group consisting of:

(a) nucleotides 145 through 489 of the DNA sequence of SEQ ID NO 1;

(b) DNA sequences that detectably hybridize to the DNA sequences of (a) or their complementary strands under conditions of high stringency and upon expression encode mammalian ETF; and (c) DNA sequences that, due to degeneracy of the genetic code, encode a polypeptide encoded by any of the foregoing DNA sequences, 3. An isolated DNA sequence according to claim 1, wherein said DNA sequence encoding a mammalian ETF polypeptide comprises a DNA sequence selected from the group consisting off (a) nucleotides 145 through 489 of the DNA sequence of SEQ ID NO 4;

(b) DNA sequences that detectably hybridize to the DNA sequences of (a) or their complementary strands under conditions of high stringency and upon expression encode mammalian ETF; and (c) DNA sequences that, due to degeneracy of the genetic code, encode a polypeptide encoded by any of the foregoing DNA sequences.

4. A recombinant expression vector comprising a DNA sequence encoding a mammalian ETF polypeptide according to claim 1.

5. A recombinant expression vector according to claim 4, wherein said DNA sequence encoding a mammalian ETF polypeptide is selected from the groups consisting of:

(a) nucleotides 145 through 489 the DNA sequence of SEQ ID NO 1;

(b) nucleotides 145 through 489 the DNA sequence of SEQ ID NO 4;

(c) DNA sequences that delectably hybridize to the DNA sequences of (a) or (b) or their complementary strands under conditions of high stringency and upon expression encode mammalian ETF; and (d) DNA sequences that, due to degeneracy of the genetic code, encode a polypeptide encoded by any of the foregoing DNA sequences.

6. A host cell transformed or transfected with an expression vector according to claim 4.

7. A host cell transformed or transfected with an expression vector according to claim 5.

8. The host cell of claim 6 wherein the host cell is selected from the group consisting of *E. coli*, Pseudomonas, Bacillis, Streptomyces, yeast, fungi, insect cells and mammalian cells.

9. The host cell of claim 8 wherein the host cell is *E. coli*.

10. The host cell of claim 8 wherein the host cell is *Saccharomyces cerevisiae*.

11. The host cell of claim 8 wherein the host cell is a mammalian cell.

12. The host cell of claim 11 wherein the host cell is Chinese hamster ovary.

13. The host cell of claim 7 wherein the host cell is selected from the group consisting of *E. coli*, Pseudomonas, Bacillus, Streptomyces, yeast, fungi, insect cells and mammalian cells.

14. The host cell of claim 13 wherein the host cell is *E. coli*.

15. The host cell of claim 13 wherein the host cell is *Saccharomyces cerevisiae*.

16. The host cell of claim 13 wherein the host cell is a mammalian cell.

17. The host cell of claim 16 wherein the host cell is Chinese hamster ovary.

18. A process for preparing an ETF polypeptide, comprising culturing a host cell according to claim 6 under conditions promoting expression and recovering a polypeptide exhibiting ETF biological activity from the culture.

19. A process for preparing an ETF polypeptide, comprising culturing a host cell according to claim 7 under conditions promoting expression and recovering a polypeptide exhibiting ETF biological activity from the culture.

20. An isolated DNA sequence encoding a precursor polypeptide of the biologically active ETF polypeptide, wherein said DNA sequence is selected from the group consisting of:

a DNA sequence encoding on expression the polypeptide defined by SEQ ID NO 2; and a DNA sequence encoding on expression the polypeptide defined by SEQ ID NO 5.

21. The isolated DNA sequence according to claim 20, wherein said DNA sequence encoding a precursor polypeptide of the biologically active ETF polypeptide is selected from the group consisting of:

the DNA sequence of SEQ ID NO 1; and the DNA sequence of SEQ ID NO 4.

* * * * *

UNITED STATES PATENT AND TRADEMARK OFFICE
CERTIFICATE OF CORRECTION

PATENT NO.    : 5,552,303
DATED         : September 3, 1996
INVENTOR(S)   : Kenneth Grabstein et al.

It is certified that error appears in the above identified patent and that said Letters Patent is hereby corrected as shown below:

In column 29, claim 1, line 60, please delete both instances of "lie" and in both instances insert therefor --Ile--.

In column 31, claim 5, line 1, please delete "delectably" and insert therefor --detectably--.

Signed and Sealed this

Eleventh Day of February, 1997

*Attest:*

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 489 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..489

( x i ) SEQUENCE DESCRIPTION: SEQ ID NO:1:

```
ATG AGA ATT TCG AAA CCA CAT TTG AGA AGT ATT TCC ATC CAG TGC TAC      48
Met Arg Ile Ser Lys Pro His Leu Arg Ser Ile Ser Ile Gln Cys Tyr
 1           5                  10                  15

CTG TGT TTA CTT CTA AAG AGT CAT TTT CTA ACT GAA GCT GGC ATT CAT      96
Leu Cys Leu Leu Leu Lys Ser His Phe Leu Thr Glu Ala Gly Ile His
             20                  25                  30

GTC TTC ATT TTG GGC TGT TTC AGT GCA GGG CTC CCT AAA ACA GAA GCC     144
Val Phe Ile Leu Gly Cys Phe Ser Ala Gly Leu Pro Lys Thr Glu Ala
         35                  40                  45

AAC TGG GTG AAT GTA ATA AGT GAT TTG AAA AAA ATT GAA GAT CTT ATT     192
Asn Trp Val Asn Val Ile Ser Asp Leu Lys Lys Ile Glu Asp Leu Ile
     50                  55                  60

CAA TCT ATG CAT ATT GAT GCT ACT TTA TAT ACA GAA AGT GAT GTT CAC     240
Gln Ser Met His Ile Asp Ala Thr Leu Tyr Thr Glu Ser Asp Val His
 65                  70                  75                  80

CCC AGT TGC AAG GTA ACA GCA ATG AAG TGC TTT CTC TTG GAG TTG CAA     288
Pro Ser Cys Lys Val Thr Ala Met Lys Cys Phe Leu Leu Glu Leu Gln
             85                  90                  95

GTT ATT TCA CAT GAG TCC GGA GAT ACA GAT ATT CAT GAT ACA GTA GAA     336
Val Ile Ser His Glu Ser Gly Asp Thr Asp Ile His Asp Thr Val Glu
            100                 105                 110

AAT CTT ATC ATC CTA GCA AAC AAC ATC TTG TCT TCT AAT GGG AAT ATA     384
Asn Leu Ile Ile Leu Ala Asn Asn Ile Leu Ser Ser Asn Gly Asn Ile
            115                 120                 125

ACA GAA TCT GGA TGC AAA GAA TGT GAG GAA CTA GAG GAA AAA AAT ATT     432
Thr Glu Ser Gly Cys Lys Glu Cys Glu Glu Leu Glu Glu Lys Asn Ile
        130                 135                 140

AAA GAA TTT TTG CAG AGT TTT GTA CAT ATT GTC CAA ATG TTC ATC AAC     480
Lys Glu Phe Leu Gln Ser Phe Val His Ile Val Gln Met Phe Ile Asn
145                 150                 155                 160

ACT TCT TGA                                                         489
Thr Ser
```

( 2 ) INFORMATION FOR SEQ ID NO:2:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ile Ser Lys Pro His Leu Arg Ser Ile Ser Ile Gln Cys Tyr
 1               5                  10                  15
Leu Cys Leu Leu Leu Lys Ser His Phe Leu Thr Glu Ala Gly Ile His
                20                  25                  30
Val Phe Ile Leu Gly Cys Phe Ser Ala Gly Leu Pro Lys Thr Glu Ala
            35                  40                  45
Asn Trp Val Asn Val Ile Ser Asp Leu Lys Lys Ile Glu Asp Leu Ile
        50                  55                  60
Gln Ser Met His Ile Asp Ala Thr Leu Tyr Thr Glu Ser Asp Val His
 65                  70                  75                  80
Pro Ser Cys Lys Val Thr Ala Met Lys Cys Phe Leu Leu Glu Leu Gln
                85                  90                  95
Val Ile Ser His Glu Ser Gly Asp Thr Asp Ile His Asp Thr Val Glu
            100                 105                 110
Asn Leu Ile Ile Leu Ala Asn Asn Ile Leu Ser Ser Asn Gly Asn Ile
            115                 120                 125
Thr Glu Ser Gly Cys Lys Glu Cys Glu Glu Leu Glu Glu Lys Asn Ile
    130                 135                 140
Lys Glu Phe Leu Gln Ser Phe Val His Ile Val Gln Met Phe Ile Asn
145                 150                 155                 160
Thr Ser
```

( 2 ) INFORMATION FOR SEQ ID NO:3:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:3:

```
Asn Trp Val Asn Val Ile Ser Asp Leu Lys Lys Ile Glu Asp Leu Ile
 1               5                  10                  15
Gln Ser Met His Ile Asp Ala Thr Leu Tyr Thr Glu Ser Asp Val His
                20                  25                  30
Pro Ser Cys Lys Val Thr Ala Met Lys Cys Phe Leu Leu Glu Leu Gln
            35                  40                  45
Val Ile Ser His Glu Ser Gly Asp Thr Asp Ile His Asp Thr Val Glu
        50                  55                  60
Asn Leu Ile Ile Leu Ala Asn Asn Ile Leu Ser Ser Asn Gly Asn Ile
 65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
```

5,552,303

-continued

Thr Ser ( 2 ) INFORMATION FOR SEQ ID NO:4:

( i ) SEQUENCE CHARACTERISTICS:
        ( A ) LENGTH: 489 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..489

( x i ) SEQUENCE DESCRIPTION: SEQ ID NO:4:

| ATG | AGA | ATT | TCG | AAA | CCA | CAT | TTG | AGA | AGT | ATT | TCC | ATC | CAG | TGC | TAC | 48 |
|---|---|---|---|---|---|---|---|---|---|---|---|---|---|---|---|---|
| Met | Arg | Ile | Ser | Lys | Pro | His | Leu | Arg | Ser | Ile | Ser | Ile | Gln | Cys | Tyr | |
| 1 | | | | 5 | | | | | 10 | | | | | 15 | | |

| TTG | TGT | TTA | CTT | CTA | AAC | AGT | CAT | TTT | CTA | ACT | GAA | GCT | GGC | ATT | CAT | 96 |
|---|---|---|---|---|---|---|---|---|---|---|---|---|---|---|---|---|
| Leu | Cys | Leu | Leu | Leu | Asn | Ser | His | Phe | Leu | Thr | Glu | Ala | Gly | Ile | His | |
| | | | 20 | | | | | 25 | | | | | 30 | | | |

| GTC | TTC | ATT | TTG | GGC | TGT | TTC | AGT | GCA | GGG | CTT | CCT | AAA | ACA | GAA | GCC | 144 |
|---|---|---|---|---|---|---|---|---|---|---|---|---|---|---|---|---|
| Val | Phe | Ile | Leu | Gly | Cys | Phe | Ser | Ala | Gly | Leu | Pro | Lys | Thr | Glu | Ala | |
| | | 35 | | | | | 40 | | | | | 45 | | | | |

| AAC | TGG | GTG | AAT | GTA | ATA | AGT | GAT | TTG | AAA | AAA | ATT | GAA | GAT | CTT | ATT | 192 |
|---|---|---|---|---|---|---|---|---|---|---|---|---|---|---|---|---|
| Asn | Trp | Val | Asn | Val | Ile | Ser | Asp | Leu | Lys | Lys | Ile | Glu | Asp | Leu | Ile | |
| | 50 | | | | | 55 | | | | | 60 | | | | | |

| CAA | TCT | ATG | CAT | ATT | GAT | GCT | ACT | TTA | TAT | ACG | GAA | AGT | GAT | GTT | CAC | 240 |
|---|---|---|---|---|---|---|---|---|---|---|---|---|---|---|---|---|
| Gln | Ser | Met | His | Ile | Asp | Ala | Thr | Leu | Tyr | Thr | Glu | Ser | Asp | Val | His | |
| 65 | | | | | 70 | | | | | 75 | | | | | 80 | |

| CCC | AGT | TGC | AAA | GTA | ACA | GCA | ATG | AAG | TGC | TTT | CTC | TTG | GAG | TTA | CAA | 288 |
|---|---|---|---|---|---|---|---|---|---|---|---|---|---|---|---|---|
| Pro | Ser | Cys | Lys | Val | Thr | Ala | Met | Lys | Cys | Phe | Leu | Leu | Glu | Leu | Gln | |
| | | | | 85 | | | | | 90 | | | | | 95 | | |

| GTT | ATT | TCA | CTT | GAG | TCC | GGA | GAT | GCA | AGT | ATT | CAT | GAT | ACA | GTA | GAA | 336 |
|---|---|---|---|---|---|---|---|---|---|---|---|---|---|---|---|---|
| Val | Ile | Ser | Leu | Glu | Ser | Gly | Asp | Ala | Ser | Ile | His | Asp | Thr | Val | Glu | |
| | | | 100 | | | | | 105 | | | | | 110 | | | |

| AAT | CTG | ATC | ATC | CTA | GCA | AAC | AAC | AGT | TTG | TCT | TCT | AAT | GGG | AAT | GTA | 384 |
|---|---|---|---|---|---|---|---|---|---|---|---|---|---|---|---|---|
| Asn | Leu | Ile | Ile | Leu | Ala | Asn | Asn | Ser | Leu | Ser | Ser | Asn | Gly | Asn | Val | |
| | | 115 | | | | | 120 | | | | | 125 | | | | |

| ACA | GAA | TCT | GGA | TGC | AAA | GAA | TGT | GAG | GAA | CTG | GAG | GAA | AAA | AAT | ATT | 432 |
|---|---|---|---|---|---|---|---|---|---|---|---|---|---|---|---|---|
| Thr | Glu | Ser | Gly | Cys | Lys | Glu | Cys | Glu | Glu | Leu | Glu | Glu | Lys | Asn | Ile | |
| | | 130 | | | | | 135 | | | | | 140 | | | | |

| AAA | GAA | TTT | TTG | CAG | AGT | TTT | GTA | CAT | ATT | GTC | CAA | ATG | TTC | ATC | AAC | 480 |
|---|---|---|---|---|---|---|---|---|---|---|---|---|---|---|---|---|
| Lys | Glu | Phe | Leu | Gln | Ser | Phe | Val | His | Ile | Val | Gln | Met | Phe | Ile | Asn | |
| 145 | | | | | 150 | | | | | 155 | | | | | 160 | |

| ACT | TCT | TGA | 489 |
|---|---|---|---|
| Thr | Ser | | |

( 2 ) INFORMATION FOR SEQ ID NO:5:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Arg | Ile | Ser | Lys | Pro | His | Leu | Arg | Ser | Ile | Ser | Ile | Gln | Cys | Tyr |
|---|---|---|---|---|---|---|---|---|---|---|---|---|---|---|---|
| 1 | | | | 5 | | | | | 10 | | | | | 15 | |

| Leu | Cys | Leu | Leu | Leu | Asn | Ser | His | Phe | Leu | Thr | Glu | Ala | Gly | Ile | His |
|---|---|---|---|---|---|---|---|---|---|---|---|---|---|---|---|
| | | | 20 | | | | | 25 | | | | | 30 | | |

```
Val  Phe  Ile  Leu  Gly  Cys  Phe  Ser  Ala  Gly  Leu  Pro  Lys  Thr  Glu  Ala
          35                       40                      45

Asn  Trp  Val  Asn  Val  Ile  Ser  Asp  Leu  Lys  Lys  Ile  Glu  Asp  Leu  Ile
     50                       55                      60

Gln  Ser  Met  His  Ile  Asp  Ala  Thr  Leu  Tyr  Thr  Glu  Ser  Asp  Val  His
65                       70                      75                            80

Pro  Ser  Cys  Lys  Val  Thr  Ala  Met  Lys  Cys  Phe  Leu  Leu  Glu  Leu  Gln
               85                       90                           95

Val  Ile  Ser  Leu  Glu  Ser  Gly  Asp  Ala  Ser  Ile  His  Asp  Thr  Val  Glu
          100                      105                     110

Asn  Leu  Ile  Ile  Leu  Ala  Asn  Asn  Ser  Leu  Ser  Ser  Asn  Gly  Asn  Val
          115                      120                     125

Thr  Glu  Ser  Gly  Cys  Lys  Glu  Cys  Glu  Glu  Leu  Glu  Glu  Lys  Asn  Ile
130                      135                     140

Lys  Glu  Phe  Leu  Gln  Ser  Phe  Val  His  Ile  Val  Gln  Met  Phe  Ile  Asn
145                      150                     155                          160

Thr  Ser
```

( 2 ) INFORMATION FOR SEQ ID NO:6:

( i ) SEQUENCE CHARACTERISTICS:
        ( A ) LENGTH: 114 amino acids
        ( B ) TYPE: amino acid
        ( D ) TOPOLOGY: linear ( i i ) MOLECULE TYPE: protein ( i i i ) HYPOTHETICAL: NO ( x i ) SEQUENCE DESCRIPTION: SEQ ID NO:6:

```
Asn  Trp  Val  Asn  Val  Ile  Ser  Asp  Leu  Lys  Lys  Ile  Glu  Asp  Leu  Ile
1                        5                       10                          15

Gln  Ser  Met  His  Ile  Asp  Ala  Thr  Leu  Tyr  Thr  Glu  Ser  Asp  Val  His
               20                      25                      30

Pro  Ser  Cys  Lys  Val  Thr  Ala  Met  Lys  Cys  Phe  Leu  Leu  Glu  Leu  Gln
          35                       40                      45

Val  Ile  Ser  Leu  Glu  Ser  Gly  Asp  Ala  Ser  Ile  His  Asp  Thr  Val  Glu
     50                       55                      60

Asn  Leu  Ile  Ile  Leu  Ala  Asn  Asn  Ser  Leu  Ser  Ser  Asn  Gly  Asn  Val
65                       70                      75                          80

Thr  Glu  Ser  Gly  Cys  Lys  Glu  Cys  Glu  Glu  Leu  Glu  Glu  Lys  Asn  Ile
               85                       90                      95

Lys  Glu  Phe  Leu  Gln  Ser  Phe  Val  His  Ile  Val  Gln  Met  Phe  Ile  Asn
          100                      105                     110

Thr  Ser
```

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

TCGACTGGAA CGAGACGACC TGCT 24

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

AGCAGGTCGT CTCGTTCCAG 20

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

AAYTGGGTNA AYGTNATH 18

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

ACRTCNGAYT CNGTRTA 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:11:

ACRTCRCTYT CNGTRTA 17

( 2 ) INFORMATION FOR SEQ ID NO:12:

( i ) SEQUENCE CHARACTERISTICS:
  ( A ) LENGTH: 114 amino acids
  ( B ) TYPE: amino acid
  ( D ) TOPOLOGY: linear ( i i ) MOLECULE TYPE: protein ( i i i ) HYPOTHETICAL: NO ( x i ) SEQUENCE DESCRIPTION: SEQ ID NO:12:

| Asn | Trp | Val | Asn | Val | Ile | Ser | Asp | Leu | Lys | Lys | Ile | Glu | Asp | Leu | Ile |
|---|---|---|---|---|---|---|---|---|---|---|---|---|---|---|---|
| 1 | | | | 5 | | | | | 10 | | | | | 15 | |
| Gln | Ser | Met | His | Ile | Asp | Ala | Thr | Leu | Tyr | Thr | Glu | Ser | Asp | Val | His |
| | | | 20 | | | | | 25 | | | | | 30 | | |
| Pro | Ser | Cys | Lys | Val | Thr | Ala | Met | Lys | Cys | Phe | Leu | Leu | Glu | Leu | Gln |
| | | 35 | | | | | 40 | | | | | 45 | | | |
| Val | Ile | Ser | Xaa | Glu | Ser | Gly | Asp | Xaa | Xaa | Ile | His | Asp | Thr | Val | Glu |
| | 50 | | | | | 55 | | | | | 60 | | | | |
| Asn | Leu | Ile | Ile | Leu | Ala | Asn | Asn | Xaa | Leu | Ser | Ser | Asn | Gly | Asn | Xaa |
| 65 | | | | | 70 | | | | | 75 | | | | | 80 |
| Thr | Glu | Ser | Gly | Cys | Lys | Glu | Cys | Glu | Glu | Leu | Glu | Glu | Lys | Asn | Ile |
| | | | | 85 | | | | | 90 | | | | | 95 | |
| Lys | Glu | Phe | Leu | Gln | Ser | Phe | Val | His | Ile | Val | Gln | Met | Phe | Ile | Asn |
| | | | 100 | | | | | 105 | | | | | 110 | | |
| Thr | Ser | | | | | | | | | | | | | | |